(12) United States Patent
Saitoh et al.

(10) Patent No.: US 6,774,245 B2
(45) Date of Patent: Aug. 10, 2004

(54) 3-HYDROXYMETHYLBENZO[B]THIOPHENE DERIVATIVES AND PROCESS FOR THEIR PREPARATION

(75) Inventors: Hiroshi Saitoh, Hino (JP); Tsuyoshi Mizuno, Hino (JP); Naoki Tsuchiya, Hino (JP)

(73) Assignee: Teijin Limited, Osaka (JP)

( * ) Notice: Subject to any disclaimer, the term of this patent is extended or adjusted under 35 U.S.C. 154(b) by 22 days.

(21) Appl. No.: 10/332,079
(22) PCT Filed: May 2, 2002
(86) PCT No.: PCT/JP02/04383
§ 371 (c)(1), (2), (4) Date: Jan. 2, 2003
(87) PCT Pub. No.: WO02/090345
PCT Pub. Date: Nov. 14, 2002

(65) Prior Publication Data
US 2003/0191325 A1 Oct. 9, 2003

(30) Foreign Application Priority Data
May 7, 2001 (JP) ........................................ 2001-135928

(51) Int. Cl.[7] ........................................... C07D 333/56
(52) U.S. Cl. ...................................................... 549/58
(58) Field of Search ........................................... 549/58

(56) References Cited

U.S. PATENT DOCUMENTS 6,495,702 B2 * 12/2002 Honma et al. ................ 549/51

FOREIGN PATENT DOCUMENTS

WO    WO 01/53291 A1    1/2001

OTHER PUBLICATIONS

Neidlein, et al., "Unterschungen zur Synthese des Schwefelisosteren Psilocins und Einiger 4–Hydroxybenzo(b-)thiophenderivate", Tetrahedron, vol. 33, pp. 3233–3237, Pergamon Press 1977.
Makisumi, Yasuo, et al., "Synthesis of Condensed Thiophens Via [2,3]and [3,3]Sigmatropic Rearrangements of Aryl Prop–2–YNYL—Sulphoxides", J.C.S. Chem. Comm., 1974, pp. 848–849.
Numata, et al., "Partial Asymmetric Pummerer Reaction of Aryl Prop–2–YNYL Sulfoxide with Acetic Anhydride", Chemistry Letters, pp. 909–912, 1977.

* cited by examiner

Primary Examiner—Deborah C. Lambkin
(74) Attorney, Agent, or Firm—Sughrue Mion, PLLC

(57) ABSTRACT

The present invention is a method of producing a 3-hydroxymethyl-benzo[b]thiophene derivative without the possible concomitant formation of isomers, which comprises selectively cyclizing a sulfoxide having X shown in the reaction scheme below:

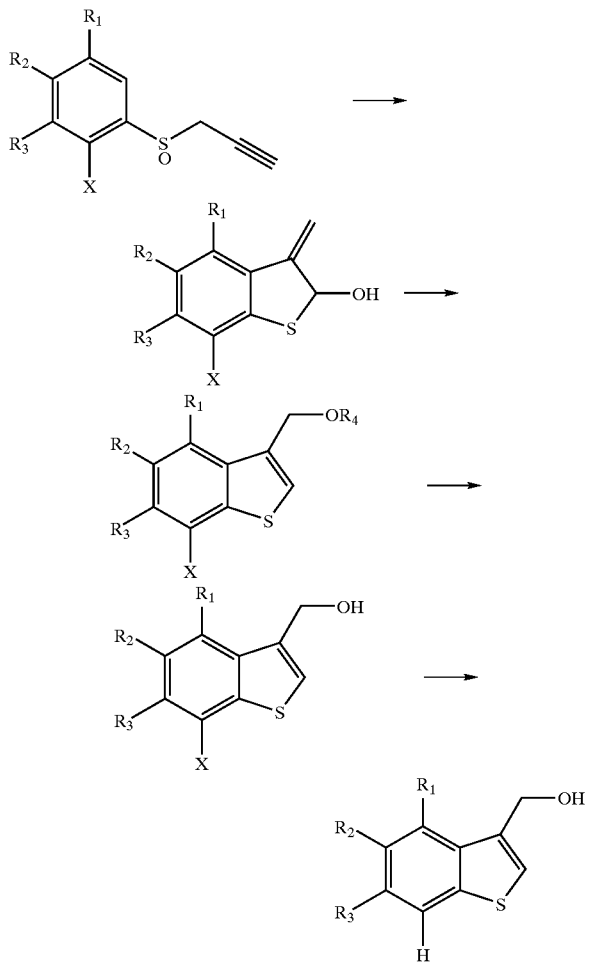

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; $R_4$ is an acyl group; X is a halogen atom, a hydroxy group, an amino group, a mercapto group, an alkylthio group having 1 to 9 carbons, an acyloxy group having 1 to 9 carbons, an acylamino group having 1 to 9 carbons, or a trihalomethoxy group.

12 Claims, No Drawings

3-HYDROXYMETHYLBENZO[B]THIOPHENE DERIVATIVES AND PROCESS FOR THEIR PREPARATION

TECHNICAL FIELD

The present invention relates to 3-hydroxymethyl-benzo[b]thiophene derivatives which are important as starting materials for the production of compounds useful in the pharmaceutical field, and methods for producing them.

BACKGROUND ART

3-Hydroxymethyl-benzo[b]thiophene derivatives represented by the formula (II):

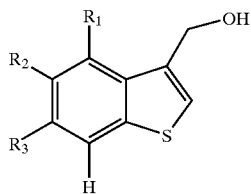

(II)

wherein, $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group, are very important as intermediates for the production of pharmacologically active compounds.

For example, a compound in which a hydroxyl group has been replaced with a bromine atom in a compound represented by the formula (II) can be a starting material for a synthetic intermediate of benzimidazole derivatives described in the specification of WO 01/53291, and can be said to be very important as an intermediate for the production of pharmacologically active compounds.

However, the production of benzothiophene derivatives having a hydroxymethyl group at the position 3 and having other substituents in a position-selective manner as in the compounds represented by the formula (II) is very difficult, and none have been suitable for industrial production. For example, there are a method in which benzo[b]thiophene is subjected to the Vilsmeier reaction etc. to synthesize 3-formyl-benzo[b]thiophene (J. Org. Chem., 72:1422 (1957)) which is then reduced, a method in which benzo[b]thiophene is subjected to the Friedel-Crafts reaction to synthesize a 3-trichloroacetyl-benzo[b]thiophene derivative (J. Chem. Soc., Perkin Trans. 2:1250 (197u3)) as a starting material candidate, which is hydrolyzed and then reduced, and the like. In any of them, however, depending on the type and the position of the originally retained substituents, at both positions 2 and 3 or any position from positions 2 to 7 on the benzo[b]thiophene ring, a substitution reaction proceeds wherein position-selectivity in the reaction highly tends to depend on the substrates and the reaction conditions used, and thus selectivity is not always high. Furthermore, the isolation of the desired compound from these mixtures is very difficult.

Furthermore, J. Chem. Soc., Chem. Comm., 848 (1974) reports a reaction in which, a propargyl group was introduced into a benzenethiol derivative, which is then subjected to an oxidation reaction to obtain a compound represented by the formula (VIII):

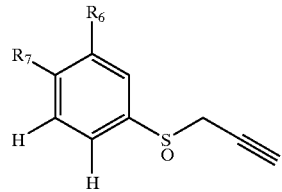

(VIII)

wherein $R_6$ and $R_7$ are all hydrogen atoms, or $R_6$ and $R_7$ together form a benzene ring, which is then subjected to a heat transfer reaction to obtain a compound represented by the formula (IX):

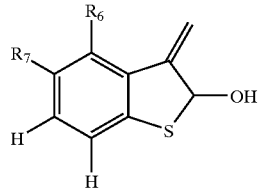

(IX)

wherein $R_6$ and $R_7$ are all hydrogen atoms, or $R_6$ and $R_7$ together form a benzene ring, which is then subjected to a heat transfer reaction in water-dioxane in the presence of p-toluenesulfonic acid to obtain a compound represented by the formula (X):

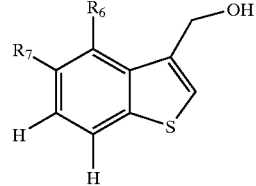

(X)

wherein $R_6$ and $R_7$ are all hydrogen atoms, or $R_6$ and $R_7$ together form a benzene ring. In this reaction, however, reaction may occur at both ortho positions of the sulfur atom in the compound represented by the formula (VIII), and thus, depending on the position of substituents on the benzene ring, the selectivity required to obtain the compound of interest may not be obtained. Thus, there may be formed the formula (XI) which is not desired, together with the formula (IX), and the formula (XII) which is not desired, together with the formula (X).

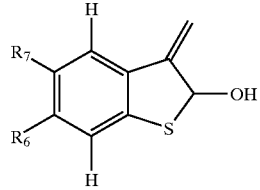

(XI)

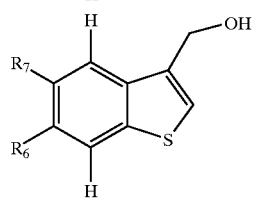

(XII)

wherein $R_6$ and $R_7$ are all hydrogen atoms, or $R_6$ and $R_7$ together form a benzene ring.

From the foregoing, there has been a need for a selective method of synthesizing 3-hydroxymethyl-benzo[b]thiophene represented by the formula (II) without the possible concomitant production of isomers.

DISCLOSURE OF THE INVENTION

It is an object of the present invention to resolve the problems encountered in the above conventional methods, and to provide a method of producing 3-hydroxymethyl-benzo[b]thiophene derivatives without the possible concomitant production of isomers.

The present invention provides a method of producing a 3-hydroxymethyl-benzo[b]thiophene derivative represented by the formula (II):

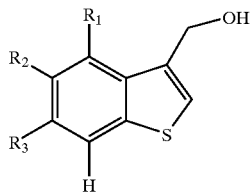

(II)

wherein, $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group, by allowing a hydrogenating agent to act on a compound represented by the formula (I):

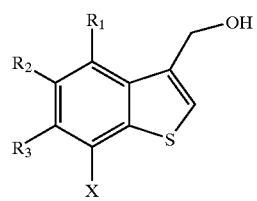

(I)

wherein, $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, thereby to attain the selective hydrogenation of the substituent X alone.

In the above method, it is preferred that $R_1$ to $R_3$ in the above formula (I) are, same or independently, a hydrogen atom, an alkyl group having 1 to 4 carbons, or a trihalomethyl group, and X is a halogen atom.

Furthermore, the present invention provides a method of producing a 3-hydroxymethyl-benzo[b]thiophene derivative represented by the above formula (II), wherein a benzo[b]thiophene derivative represented by the above formula (I) is produced by reducing a compound represented by the formula (IV):

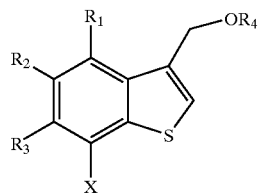

(IV)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_4$ is an acyl group, with a hydrogenating metal complex compound, basic hydrolysis, or acid hydrolysis.

Furthermore, the present invention provides a method of producing a 3-hydroxymethyl-benzo[b]thiophene derivative represented by the above formula (II), wherein a benzo[b]thiophene derivative represented by the above formula (IV) is produced by reacting a compound represented by the formula (III):

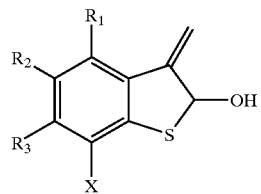

(III)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, with one or more of carboxylic acid anhydride or carboxylic acid.

Furthermore, the present invention provides a method of producing a 3-hydroxymethyl-benzo[b]thiophene derivative represented by the above formula (II), wherein a compound represented by the above formula (III) is produced by the following steps (1) to (3):

(1) a step of reacting a propargyl group to a compound represented by the formula (V):

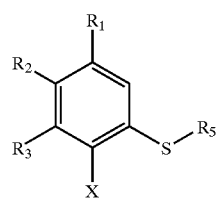

(V)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_5$ is an alkoxythiocarbonyl group, an alkyl group, a hydrogen atom, a halogen atom, a sodium atom, a lithium atom, a potassium atom, a magnesium atom, or a calcium atom, in a substitution reaction to obtain a compound represented by the formula (VI):

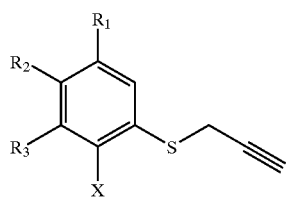

(VI)

wherein $R_1$ to $R_3$ and X are as defined in the above formula (V);

(2) a step of oxidizing a compound represented by the formula (VI) to obtain a compound represented by the formula (VII):

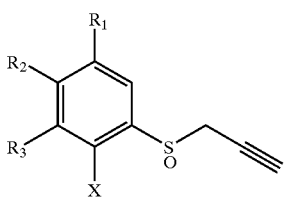

(VII)

wherein $R_1$ to $R_3$ and X are as defined in the above formula (V); and (3) a step of obtaining a compound represented by the formula (III) by subjecting a compound represented by the above formula (VII) to a heat transfer reaction.

Furthermore, the present invention provides a 3-hydroxymethyl-benzo[b]thiophene derivative represented by the formula (II):

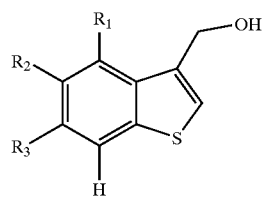

(II)

wherein $R_1$ and $R_2$ are, same or independently, an alkyl group having 1 to 4 carbons, and $R_3$ is a hydrogen atom.

Furthermore, the present invention provides a method of producing a 3-hydroxymethyl-benzo[b]thiophene derivative represented by the formula (I):

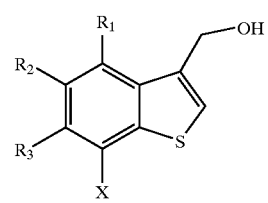

(I)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, characterized in that a compound represented by the formula (IV):

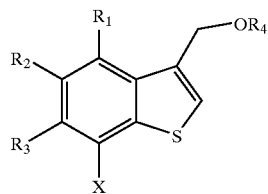

(IV)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_4$ is an acyl group, is reduced with a hydrogenating metal complex compound, basic hydrolysis, or acid hydrolysis.

Furthermore, the present invention provides a 3-hydroxymethyl-benzo[b]thiophene derivative represented by the formula (I):

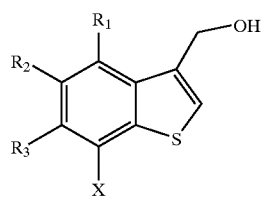

(I)

wherein $R_1$ is an alkyl group having 1 to 4 carbons, a trihalomethyl group, an alkoxy group having 1 to 4 carbons, an alkylthio group having 1 to 4 carbons, or a trihalomethoxy group; $R_2$ and $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom.

In the above formula (I), a 3-hydroxymethyl-benzo[b]thiophene derivative
wherein X is a halogen atom, $R_1$ is an alkyl group having 1 to 4 carbons, and each of $R_2$ and $R_3$ is a hydrogen atom; or
X is a halogen atom, $R_1$ and $R_2$ are, together or independently, an alkyl group having 1 to 4 carbons, and $R_3$ is a hydrogen atom, is preferable.

Furthermore, the present invention provides a method of producing a 3-hydroxymethyl-benzo[b]thiophene derivative represented by the formula (IV):

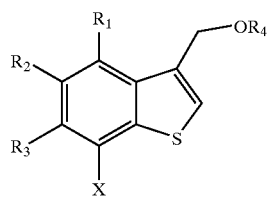

(IV)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_4$ is an acyl group, by reacting a compound represented by the formula (III):

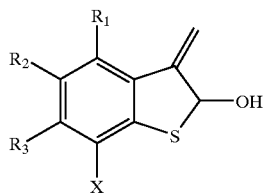

(III)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, with one or more of carboxylic acid anhydride or carboxylic acid.

In said method of production, preferably, $R_1$ to $R_3$ are, same or independently, a hydrogen atom, an alkyl group having 1 to 4 carbons, or a trihalomethyl group; and X is a halogen atom in the above formula (III).

Furthermore, the present invention provides a benzo[b]thiophene derivative represented by the formula (IV):

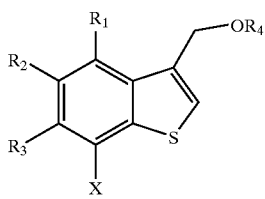

(IV)

wherein X is a halogen atom, $R_4$ is a trifluoroacetyl group, and $R_1$ is an alkyl group having 1 to 4 carbons, $R_2$ and $R_3$ are a hydrogen atom, or $R_1$ and $R_2$ are, together or independently, an alkyl group having 1 to 4 carbons, and $R_3$ is a hydrogen atom.

EMBODIMENT FOR CARRYING OUT THE INVENTION

In accordance with the present invention, it is preferred that a compound represented by the formula (III):

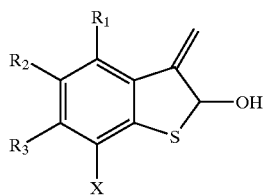

(III)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, is reacted with one or more of carboxylic acid anhydride or carboxylic acid to obtain a compound represented by the formula (IV):

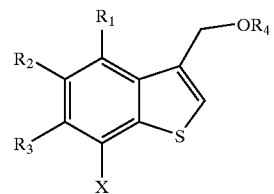

(IV)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_4$ is an acyl group, $R_4$ of the compound (IV) is replaced with a hydroxyl group to obtain a compound represented by the formula (I):

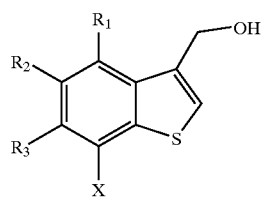

(I)

wherein, $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, and then the substituent X of a compound represented by the formula (I) is subjected to a selective hydrogen-substitution reaction to produce a 3-hydroxymethyl-benzo[b]thiophene derivative represented by the formula (II):

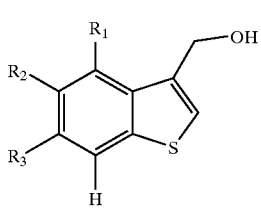

(II)

wherein, $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group.

$R_1$ to $R_3$ in the formula of the present invention are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group. Preferably, $R_1$ to $R_3$ are, same or independently, a hydrogen atom, an alkyl group having 1 to 4 carbons, a trihalomethyl group, a halogen atom, and most preferably a hydrogen atom or an alkyl group having 1 to 4 carbons $R_4$ in the formula is an acyl group. $R_4$ is preferably a trifluoroacetyl group or an acetyl group, and more preferably a trifluoroacetyl group.

X in the formula is a halogen atom, a hydroxy group, or an acyloxy group having 1 to 9 carbons. X is preferably a bromine atom or a chlorine atom, and more preferably a bromine atom.

In preferred combinations of $R_1$, $R_2$ and $R_3$, $R_1$ and $R_3$ are not the same. In more preferred combinations of $R_1$, $R_2$ and $R_3$, $R_1$ is an alkyl group having 1 to 4 carbons, $R_2$ and $R_3$ are a hydrogen atom, or $R_1$ and $R_2$ are an alkyl group having 1 to 4 carbons and $R_3$ is a hydrogen atom. In more preferred combinations of $R_1$, $R_2$ and $R_3$, $R_1$ is a methyl group or an ethyl group, and $R_2$ and $R_3$ are a hydrogen atom; or $R_1$ and $R_2$ are a methyl group or an ethyl group, and $R_3$ is a hydrogen atom. In particularly more preferred combinations of $R_1$, $R_2$ and $R_3$, $R_1$ is a methyl group and $R_2$ and $R_3$ are a hydrogen atom.

As examples of preferred combinations of $R_1$, $R_2$ and $R_3$, the following are specifically illustrated.

Preferred compounds of compound (III) are 7-bromo-4-methyl-3-methylene-2-hydro-benzo[b]thiophene-2-ol, 7-chloro-4-methyl-3-methylene-2-hydro-benzo[b]thiophene-2-ol, 7-bromo-4,5-dimethyl-3-methylene-2-hydro-benzo[b]thiophene-2-ol, 7-chloro-4,5-dimethyl-3-methylene-2-hydro-benzo[b]thiophene-2-ol, 7-bromo-4-ethyl-3-methylene-2-hydro-benzo[b]thiophene-2-ol, and 7-chloro-4-ethyl-3-methylene-2-hydro-benzo[b]thiophene-2-ol. More preferably, they are 7-bromo-4-methyl-3-methylene-2-hydro-benzo[b]thiophene-2-ol and 7-chloro-4-methyl-3-methylene-2-hydro-benzo[b]thiophene-2-ol. A more preferred compound (III) is 7-bromo-4-methyl-3-methylene-2-hydro-benzo[b]thiophene-2-ol.

Preferred compounds of compound (IV) are (7-bromo-4-methylbenzo[b]thiophene-3-yl)methyl trifluoroacetate, (7-chloro-4-methylbenzo[b]thiophene-3-yl)methyl trifluoroacetate, (7-bromo-4,5-dimethylbenzo[b]thiophene-3-yl)methyl trifluoroacetate, (7-chloro-4,5-dimethylbenzo[b]thiophene-3-yl)methyl trifluoroacetate, (7-bromo-4-ethylbenzo[b]thiophene-3-yl)methyl trifluoroacetate, and (7-chloro-4-ethylbenzo[b]thiophene-3-yl)methyl trifluoroacetate. More preferred compounds (IV) are (7-bromo-4-methylbenzo[b]thiophene-3-yl)methyl trifluoroacetate and (7-chloro-4-methylbenzo[b]thiophene-3-yl)methyl trifluoroacetate. A most preferred compound (IV) is (7-bromo-4-methylbenzo[b]thiophene-3-yl)methyl trifluoroacetate.

Preferred compounds of compound (I) are 7-bromo-3-hydroxymethyl-4-methyl-benzo[b]thiophene, 7-chloro-3-hydroxymethyl-4-methyl-benzo[b]thiophene, 7-bromo-3-hydroxymethyl-4,5-dimethyl-benzo[b]thiophene, 7-chloro-3-hydroxymethyl-4,5-dimethyl-benzo[b]thiophene, 7-bromo-3-hydroxymethyl-4-ethyl-benzo[b]thiophene, and 7-chloro-3-hydroxymethyl-4-ethyl-benzo[b]thiophene, and preferred compounds of compound (II) are 3-hydroxymethyl-4-methylbenzo[b]thiophene, 3-hydroxymethyl-4-ethylbenzo[b]thiophene, and 3-hydroxymethyl-4,5-dimethylbenzo[b]thiophene. More preferred compounds of compound (I) are 7-bromo-3-hydroxymethyl-4-methyl-benzo[b]thiophene and 7-chloro-3-hydroxymethyl-4-methyl-benzo[b]thiophene. A particularly more preferred compound of compound (I) is 7-bromo-3-hydroxymethyl-4-methyl-benzo[b]thiophene.

In the hydrogen substitution reaction from formula (I) to (II) in the present invention, the reaction is effected with sodium hydrogenated bis(2-methoxyethoxy)aluminum, lithium aluminum hydride, hydrogen/palladium carbon/magnesium, hydrogen/palladium carbon/triethylamine, hydrogen/palladium carbon-ethylenediamine complex/triethylamine, and the like. In preferred methods, reaction is effected with sodium hydrogenated bis(2-methoxyethoxy) aluminum, lithium aluminum hydride, and hydrogen/palladium carbon/triethylamine.

Solvents for use in the hydrogen substitution reaction from formula (I) to (II) preferably include, but not limited to, toluene, THF, diethylether, methanol, ethanol, isopropyl alcohol, and the like.

The reaction temperature in the reaction from formula (I) to formula (II) of the present invention is carried out preferably at 0° C. to 80° C.

Particularly preferred conditions include a reaction of a compound (I) and a four-fold amount of hydrogenated bis(2-methoxyethoxy)aluminum in a molar ratio relative to the compound (I) in toluene-THF at 70° C. for 3 hours; a reaction of a compound (I) and a four-fold amount of lithium aluminum hydride in a molar ratio relative to the compound (I) in THF at 70° C. for 36 hours; or a reaction of a compound (I) and a 0.10-fold amount of palladium carbon in a molar ratio relative to the compound (I), and a 1.2-fold amount of triethylamine in a molar ratio relative to the compound (I) in a methanol solvent at a hydrogen atmosphere at 50° C. for 24 hours.

Methods of synthesizing compounds represented by the formula (I) of the present invention include, but not limited to, those methods mentioned below. It should be noted, however, that the following reaction conditions differ with the properties of the substrates used and hence are not limited to the following conditions in any way.

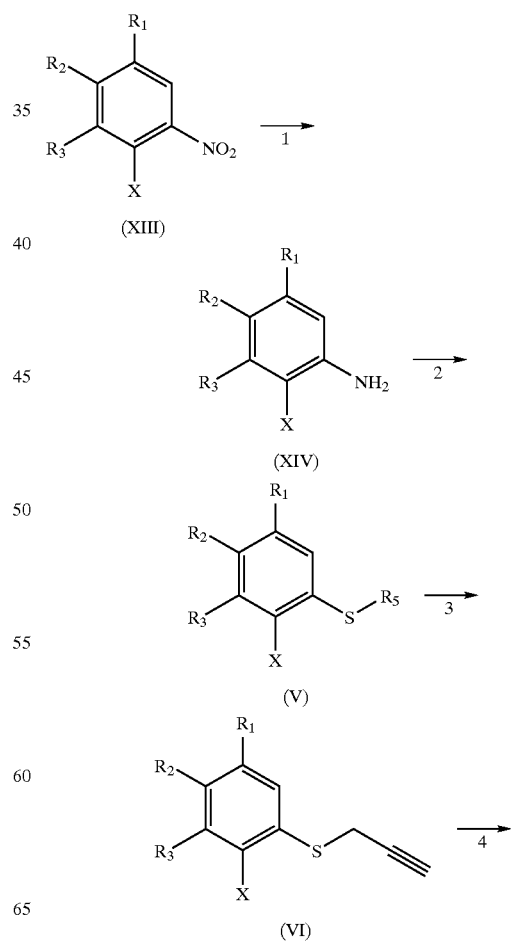

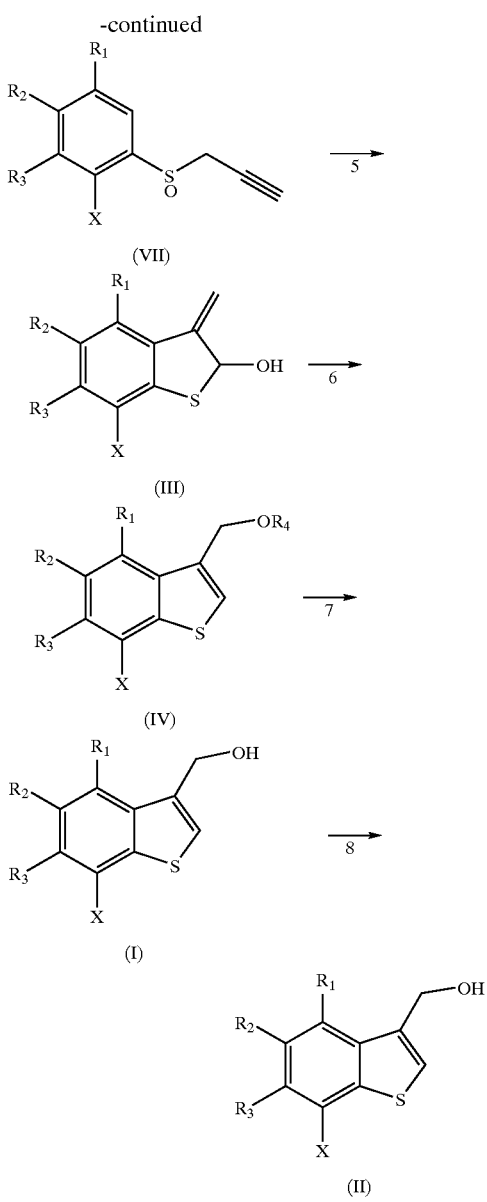

The definition of $R_1$, $R_2$, $R_3$, $R_4$, $R_5$ and X used in the above scheme are as described below. $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; $R_4$ is an acyl group; $R_5$ is an alkoxythiocarbonyl group, an alkyl group, a hydrogen atom, a halogen atom, a sodium atom, a lithium atom, a potassium atom, a magnesium atom, or a calcium atom; and X is a halogen atom, a hydroxy atom, or an acyloxy group having 1 to 9 carbons.

The steps represented by 1 to 8 in the above scheme are now explained in detail.

(Step 1)

In this step, the nitro group in the substituted nitrobenzene (XIII) is selectively reduced to produce a compound represented by the formula (XIV). The reaction of this step can be accomplished by stirring hydrochloric acid and tin dichloride in acetic acid at room temperature to 60° C. for 8 to 12 hours. The reaction of this step can also be accomplished by stirring in the presence of hydrazine monohydrate and the Raney Nickel catalyst in a solvent such as methanol, ethanol or THF at room temperature to the reflux temperature for 8 to 12 hours. The reaction of this step can also be accomplished by stirring in the presence of a platinum carbon catalyst in formic acid and triethylamine at 100° C. for 3 to 12 hours.

(Step 2)

In this step, the substituted aniline (XIV) is converted to a diazonium salt, to which various alkoxydithiocarbonates or thiolate are reacted to obtain a benzenethiol derivative (V). It is reacted as an aqueous solution of hydrochloric acid with sodium nitrite at the range of 0–10° C. to convert the substituted aniline to a diazonium salt. The method of changing the diazonium into alkoxy dithio carbonate preferably uses potassium O-ethyldithio carbonate, and the reaction temperature is 40° C. to 50° C., preferably 45° C. to 50° C. for 1 to 2 hours.

(Step 3)

In this step, in stead of the alkoxycarbonyl of the benzenethiol derivative (V), a propargyl group is subjected to a substitution reaction to obtain a compound represented by the formula (VI). The introduction of the propargyl group can be accomplished with a halogenated propargyl, for example propargyl bromide or propargyl chloride using a basic substance such as N,N-dimethylethylenediamine, ethylenediamine, 2-aminoethylmorpholine, or methylamine in a solvent such as acetone, tetrahydrofuran, 2-butanone, methanol, ethanol or isopropyl alcohol at –20° C. to 30° C. in 1 to 2 hours.

(Step 4)

In this step, a sulfide derivative (VI) is oxidized to a sulfoxide derivative (VII). In this step, preferably 1.05 equivalent of Oxone, and 0.1 equivalent of acetone, a 0.05 equivalent of phase-transfer catalyst such as tetrabutyl ammonium bromide or tetrabutyl ammonium chloride are stirred in the solvent system of ethyl acetate-water at 0° C. to 30° C. for 6 hours to 25 hours. In this step also, 1.2 equivalent of sodium metaperiodate is stirred in the solvent system of alcohol (e.g. methanol, ethanol, or isopropanol)-water at room temperature for several hours.

(Step 5)

In this step, a compound represented by the formula (III) is synthesized by a transfer cyclization reaction of a sulfoxide derivative (VII). For the transfer cyclization reaction of the present invention, reference is made to the method described in J.C.S. Chem. Comm., 848–849, 1974. For the sulfoxide for use in the present invention, preferred solvents include ethyl acetate, propyl acetate, isopropyl acetate, dimethoxyethane, 2-butanone, dioxane and the like. Preferably the amount of the solvent required is, but not limited to, more than 10 times the weight of the substrate, more preferably 15 to 25 times the weight of the substrate. By reacting this amount of the solvent, the production of byproducts can be suppressed at the minimum level and the yield can thus be enhanced. The reaction is preferably carried out at the reaction temperature of 60° C. to 100° C., and preferably 80° C. to 90° C. When the reaction is carried out at the reflux temperature, it will be complete in 30 minutes to 3 hours.

(Step 6)

In this step, the cyclized product (III) obtained in step 5 is reacted to a carboxylic acid anhydride or carboxylic acid to produce a compound represented by the formula (IV).

The solvent used in this step is the reaction solvent used in step 5, but without being concentrated, and to the reaction system a carboxylic acid anhydride or a carboxylic acid is merely added thereby to obtain a 3-alkylcarbonylmethylbenzo[b]thiophene derivative or a 3-hydroxymethylbenzo[b]thiophene derivative. A similar reaction will proceed when the solvent in step 5 is concentrated and is reacted in a different solvent. The carboxylic acid anhydride or the carboxylic acid to be added in this reaction is one or more than one, and as the carboxylic acid anhydride trifluoroacetic acid anhydride or acetic anhydride is preferred, and as carboxylic acid trifluoroacetic acid anhydride or acetic acid is preferred.

The reaction temperature in this reaction is 0° C. to 50° C., preferably 0° C. to 30° C. The reaction will be complete in scores of minutes to several hours.

(Step 7)

In this step, the carboxylic acid ester, if obtained in step 6, is hydrolyzed to obtain a 3-hydroxymethyl-benzo[b] thiophene derivative (I). The reaction is carried out using tetrahydrofuran, methanol, ethanol, or isopropyl alcohol as the solvent, and to the carboxylic acid ester an aqueous solution of sodium hydroxide or sodium borohydride is reacted. The reaction will be complete at a temperature of 0° C. to 30° C. in several hours. As the reaction solvent, tetrahydrofuran-methanol may be mentioned.

(Step 8)

In this step, a compound represented by the formula (II) is produced by the hydrogenation reaction of position 7 of 3-hydroxymethyl-benzo[b]thiophene derivative (I).

The hydrogenating agent used is sodium hydrogenated bis(2-methoxyethoxy)aluminum, lithium aluminum hydride, hydrogen/palladium carbon/magnesium, hydrogen/palladium carbon/triethylamine, hydrogen/palladium carbon-ethylenediamine complex/triethylamine, or the like. Preferred are sodium hydrogenated bis(2-methoxyethoxy) aluminum, lithium aluminum hydride, or hydrogen/palladium carbon/triethylamine.

The solvent for use in this step preferably includes, but not limited to, toluene, THF, diethylether, methanol, ethanol, isopropyl alcohol or the like. The reaction of this step may preferably be carried out at a temperature of 0° C. to 80° C.

By replacing, with a bromine atom, the hydroxy group of 3-hydroxymethyl-benzo[b]thiophene derivative of the formula (II) produced in the above method, a 3-bromomethyl-benzo[b]thiophene derivative can be synthesized. The condition of the substitution reaction from the hydroxy group to the bromine atom is preferably, but not limited to, a reaction using a known phosphorus tribromide. By using the bromo product obtained, a benzimidazole derivative useful as a pharmaceutical composition may be synthesized according to a method described in, for example, WO01/53291.

EXAMPLES

The examples of the present invention will now be explained below, but it should be noted that the present invention is not limited by these examples.

Production Example 1

Synthesis of 2-bromo-5-methylaniline

4-Bromo-3-nitrotoluene (60.35 g, 279 mmol), 5% by weight platinum carbon (1.09 g, 0.28 mmol) and triethylamine (112.93 g, 1116 mmol) were stirred under heating at 100° C., to which formic acid (99%) (42.39 g, 921 mmol) was added dropwise over 20 minutes. After stirring for 12 hours, it was brought back to room temperature, and then 100 ml of ethyl acetate and 100 ml of water were added thereto. After stirring well, it was filtered through celite to remove platinum carbon. By further adding 200 ml of ethyl acetate and 100 ml of water, it was extracted, the organic phase was washed with water (300 ml×3 times), and dried on magnesium sulfate. The solvent was evaporated to obtain 2-bromo-5-methylaniline (51.30 g, 276 mmol). The yield was 99%.

$^1$H-NMR (270 MHz, CDCl$_3$) δ (ppm): 7.260 (1H, d), 6.583 (1h<d), 6.439 (1H, dq), 3.991 (2H, s), 2.221 (3H, s)

Production Example 2.

Synthesis of (2-bromo-5-methylphenylthio)ethoxymethane-1-thione

To 2-bromo-5-methylaniline (51.11 g, 275 mmol), 275 ml of water was added, and then 6N aqueous hydrochloric acid (97.0 ml, 578 mmol) was slowly added dropwise, and stirred at room temperature for 15 minutes (exothermic). The solution was stirred in an ice bath for 20 minutes, to which 55 g of ice was further added, and the internal temperature was set at 0° C. An aqueous solution (150 ml) of sodium nitrite (19.94 g, 289 mmol) was added thereto over 15 minutes, and stirred as it is kept in the ice bath over 15 minutes. This was termed as solution A. On the other hand, an aqueous solution (200 ml) of potassium ethylxanthogenate (52.90 g, 330 mmol) was prepared by keeping in an oil bath at 50° C. This was termed as solution B. To solution B, solution A which was had been at 0° C. was slowly added dropwise over 70 minutes. At this time, the addition was effected while confirming the evolution of nitrogen gas. A reddish brown reaction product formed in the bottom layer of the aqueous phase. For further 2 hours after the completion of the addition, the solution was stirred at an oil bath temperature of 55° C., and the reaction mixture was brought back to room temperature, to which ethyl acetate (300 ml) was added and extracted. Furthermore, the aqueous phase was extracted with ethyl acetate (200 ml). The organic phases extracted with ethyl acetate were combined, and after washing with water (200 ml×2 times), it was dried on magnesium sulfate. The solvent was evaporated to obtain (2-bromo-5-methylphenylthio)ethoxymethane-1-thione (80.45 g, 276 mmol). The yield was 100%.

$^1$H-NMR (270 MHz, CDCl$_3$) δ (ppm): 7.578 (1H, m), 7.422 (1H, m), 7.100 (1H, m), 4.697 and 4.610 (2H, q), 2.331 and 2.312 (3H, s), 1.429 and 1.328 (3H, s)

Example 1

Synthesis of 1-bromo-4-methyl-2-(prop-2-inylthio)benzene

To a solution of (2-bromo-5-methylphenylthio) ethoxymethane-1-thione (80.23 g, 275 mmol) in ethanol-THF (2/1) (420 ml), a solution of propargyl bromide (49.13 g, 413 mmol) in ethanol (140 ml) was slowly added dropwise in an ice bath and stirred in an ice bath for 20 minutes. Furthermore, while keeping the mixture in the ice bath, a solution of N,N-dimethylethylenediamine (48.48 g, 550 mmol) in ethanol (275 ml) was added dropwise over 15 minutes. The mixture was kept in the ice bath for 20 minutes, and removed from the ice bath and left at room temperature for 1 hour, followed by further stirring at 30° C. in an oil bath for 2 hours. To a separatory funnel that contained 2N aqueous hydrochloric acid (600 ml) and hexane (500 ml), the reaction mixture was added and extracted as it was. The aqueous phase was extracted with hexane (300 ml), and the organic phase combined was washed with 1N aqueous hydrochloric acid (200 ml). Then, after washing with water (200 ml×2 times), it was dried on magnesium sulfate. The solvent was evaporated to obtain 1-bromo-4-methyl-2-(prop-2-inylthio)benzene (62.35 g, 259 mmol). The yield was 94%.

$^1$H-NMR (270 MHz, CDCl$_3$) δ (ppm): 7.430 (1H, d), 7.257 (1H, s), 6.895 (1H, m), 3.649 (2H, s), 2.322 (3H, s), 2.246 (1H, t).

Example 2
Synthesis of 1-bromo-4-methyl-2-(prop-2-inylsulfinyl) benzene

To a solution of 1-bromo-4-methyl-2 prop-2-inylthiobenzene (62.18 g, 258 mmol), acetone (1.50 g, 25.8 mmol) and tetrabutylammonium bromide (4.16 g, 12.9 mmol) in ethyl acetate (750 ml), an aqueous solution of Oxone (166.6 g, 271 mmol) (750 ml) was added, and vigorously stirred for 21 hours. Water (250 ml) was added thereto to dissolve salts in the aqueous phase, and the aqueous phase was removed and the organic phase was washed with water (300 ml×3 times). The mixture was further washed twice with a mixture of saturated baking soda solution (100 ml) and water (200 ml), and was washed again with water (300 ml×2 times). After drying on magnesium sulfate, the solvent was evaporated to obtain 1-bromo-4-methyl-2-(prop-2-inylsulfinyl)benzene (63.37 g, 239 mmol (a value obtained by subtracting the weight of residual ethyl acetate from $^1$H NMR integrated ratio)). The yield was 93%.

$^1$H-NMR (270 MHz, CDCl$_3$) δ(ppm): 7.728 (1H, s), 7.445 (1H, d), 7.236 (1H, m), 3.875 (2H, m), 2.420 (3H, s), 2.361 (1H, t).

Example 3
Synthesis of 7-bromo-4-methyl-3-methylene-2-hydro-benzo[b]thiophene-2-ol In an oil bath at 85° C., ethyl acetate (800 ml) was brought to reflux, to which a solution of 1-bromo-4-methyl-2-(prop-2-inylsulfinyl)benzene (63.53 g, 239 mmol) in ethyl acetate (150 ml) was added dropwise over 15 minutes. After the dropwise addition, it was stirred for 2 hours in an oil bath at 85° C. to obtain 7-bromo-4-methyl-3-methylene-2-hydro-benzo[b]thiophene-2-ol. 7-bromo-4-methyl-3-methylene-2-hydro-benzo[b]thiophene-2-ol was not isolated and was transferred to the subsequent reaction as it was.

Example 4
Synthesis of (7-bromo-4-methylbenzo[b]thiophene-3-yl) methyl trifluoroacetate A solution of 7-bromo-4-methyl-3-methylene-2-hydro-benzo[b]thiophene-2-ol in ethyl acetate was brought back to 25° C., to which trifluoroacetic anhydride (50.2 g, 239 mmol) was further added dropwise. Furthermore, it was stirred for 20 minutes in an ice bath. The reaction mixture was slowly added dropwise to a saturated aqueous solution of sodium bicarbonate (400 ml) kept in an water bath, and stirred for 10 minutes in a water bath. The ethyl acetate phase was extracted as it was, and was washed with water (300 ml×2 times). After drying on magnesium sulfate, the solvent was evaporated to obtain (7-bromo-4-methylbenzo[b]thiophene-3-yl)methyl trifluoroacetate (74.76 g, 200 mmol (a value obtained by subtracting the weight of residual ethyl acetate from $^1$H NMR integrated ratio)). The yield was 84%.

$^1$H-NMR (270 MHz, CDCl$_3$) δ (ppm): 7.671 (1H, s), 7.428 (1H, d), 7.081 (1H, m), 5.659 (2H, s), 2.698 (3H, s).

Example 5
Synthesis of 7-bromo-3-hydroxymethyl-4-methyl-benzo[b]thiophene

To a solution of sodium borohydride (2.78 g, 100 mmol) in THF (200 ml), a solution of (7-bromo-4-methylbenzo[b]thiophene-3-yl)methyl trifluoroacetate (74.46 g, 199 mmol) in THF (100 ml) was added at room temperature, and stirred at room temperature. The reaction vessel containing the reaction mixture was placed in an ice bath, to which methanol (30 ml) was slowly added dropwise. It was stirred for 10 minutes as it was in the ice bath, and water (600 ml) was added the reaction mixture. The reaction mixture was transferred to a separatory funnel and 1200 ml of hexane was added thereto. On shaking the separatory funnel, a sludgy black substance formed at the bottom of the aqueous phase, which was removed. After further washing the organic phase with water (300 ml×6 times), the organic phase was dried on magnesium sulfate and the solvent was evaporated to obtain an orange solid 7-bromo-3-hydroxymethyl-4-methyl-benzo[b]thiophene (46.13 g, 179 mmol). The yield was 90%.

$^1$H-NMR (270 MHz, CDCl$_3$) δ (ppm): 7.481 (1H, s), 7.380 (1H, d), 7.034 (1H, m), 4.990 (2H, s), 2.758 (3H, s).

Example 6
Synthesis of 3-hydroxymethyl-4-methyl-benzo[b]thiophene

A solution of 7-bromo-3-hydroxymethyl-4-methyl-benzo[b]thiophene (45.91 g, 179 mmol) in toluene-THF (5/1, 220 ml) was placed in an ice bath, to which a solution of 3.4 M sodium hydrogenated bis(2-methoxyethoxy)aluminum in toluene (215 ml, 731 mmol) was added dropwise over 30 minutes. After the dropwise addition was complete, the reaction mixture was stirred at 70° C. for 3 hours, and it was brought back to room temperature and placed in an ice bath, to which ethyl acetate (300 ml) was slowly added dropwise. After stirring in the ice bath for 5 minutes, water (600 ml) was slowly added dropwise. The internal temperature increased from 17° C. to 35° C. To the reaction mixture, 1 L of water and 500 ml of ethyl acetate were added, and extracted. The aqueous phase was further extracted with 300 ml of ethyl acetate, and the combined organic phase was washed with water (300 ml×6 times). After drying the organic phase on magnesium sulfate, the solvent was evaporated to obtain pale orange crude crystals 3-hydroxymethyl-4-methyl-benzo[b]thiophene (30.80 g, 173 mmol). The yield was 97%.

The crude crystals 3-hydroxymethyl-4-methyl-benzo[b]thiophene (30.72 g, 173 mmol) obtained were dissolved in 25 ml of ethyl acetate at 80° C., to which 150 ml of hexane was further added dropwise. While stirring the solution, the heating of the oil bath was stopped, and gradually cooled. After 6 hours when it was cooled to room temperature, white crystals appeared, which were filtered and washed with hexane-ethyl acetate (10/1) (100 ml). By lyophilization, white crystals 3-hydroxymethyl-4-methyl-benzo[b]thiophene (14.43 g, 81.1 mmol) were obtained. The yield of recrystalization was 47%.

$^1$H-NMR (270 MHz, CDCl$_3$) δ (ppm): 7.695 (1H, d), 7.406 (1H, s), 7.245 (1H, m), 7.139 (1H, m), 5.012 (2H, s), 2,795 (3H, s).

Industrial Applicability

The present invention permits an efficient production of 3-hydroxymethyl-benzo[b]thiophene derivatives which are important as starting materials for pharmaceuticals with an extraordinarily high selectivity, and thus it has a very great industrial value. Furthermore, the present invention permits a highly selective synthesis of desired compounds in relatively short steps and in a simple manner from aniline derivatives or nitrobenzene derivatives having a wide variety of choices in terms of the position and the type of substituents at the level of commercially available reagents, and thus has a high potential of industrial applicability.

What is claimed is:

1. A method of producing a 3-hydroxymethyl-benzo[b]thiophene derivative represented by the formula (II):

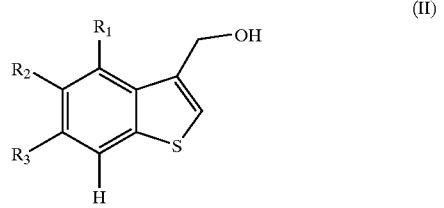

wherein, $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group, comprising reacting a hydrogenating agent with a compound represented by the formula (I):

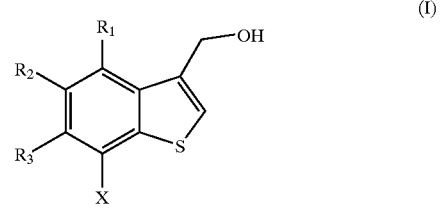

wherein, $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, thereby to attain the selective hydrogenation of the substituent X alone.

2. The method of producing a 3-hydroxymethyl-benzo[b]thiophene derivative according to claim 1 wherein $R_1$ to $R_3$ in the above formula (I) are, same or independently, a hydrogen atom, an alkyl group having 1 to 4 carbons, or a trihalomethyl group, and X is a halogen atom.

3. A method of producing a 3-hydroxymethyl-benzo[b]thiophene derivative represented by the above formula (II), wherein a benzo[b]thiophene derivative represented by the above formula (I) is produced by reducing a compound represented by the formula (IV):

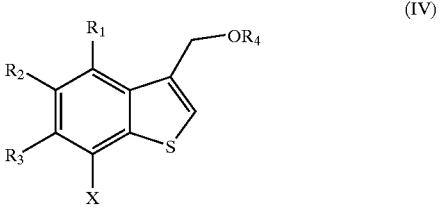

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_4$ is an acyl group, with a hydrogenating metal complex compound, basic hydrolysis, or acid hydrolysis.

4. The method of producing a 3-hydroxymethyl-benzo[b]thiophene derivative represented by the above formula (II) according to claim 3 wherein a benzo[b]thiophene derivative represented by the above formula (IV) is produced by reacting a compound represented by the formula (III):

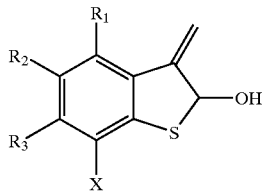

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, with one or more of carboxylic acid anhydride or carboxylic acid.

5. A method of producing a 3-hydroxymethyl-benzo[b]thiophene derivative represented by the above formula (II) according to claim 4, wherein a compound represented by the above formula (III) is produced by the following steps (1) to (3) of:

(1) reacting a propargyl group to a compound represented by the formula (V):

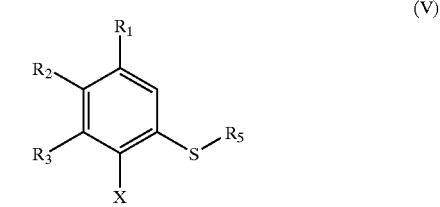

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_5$ is an alkoxythiocarbonyl group, an alkyl group, a hydrogen atom, a halogen atom, a sodium atom, a lithium atom, a potassium atom, a magnesium atom, or a calcium atom, in a substitution reaction to obtain a compound represented by the formula (VI):

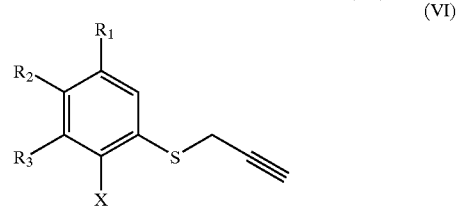

wherein $R_1$ to $R_3$ and X are as defined in the above formula (V);

(2) oxidizing a compound represented by the formula (VI) to obtain a compound represented by the formula (VII):

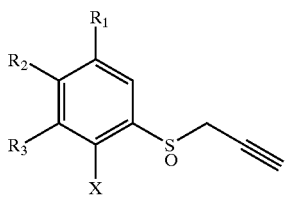

(VII)

wherein $R_1$ to $R_3$ and X are as defined in the above formula (V); and (3) obtaining a compound represented by the formula (III) by subjecting a compound represented by the above formula (VII) to a heat transfer reaction.

6. A 3-hydroxymethyl-benzo[b]thiophene derivative represented by the formula (II):

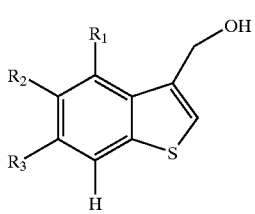

(II)

wherein $R_1$ and $R_2$ are, same or independently, an alkyl group having 1 to 4 carbons, and $R_3$ is a hydrogen atom.

7. A method of producing a 3-hydroxymethyl-benzo[b] thiophene derivative represented by the formula (I):

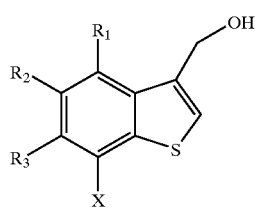

(I)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, characterized in that a compound represented by the formula (IV):

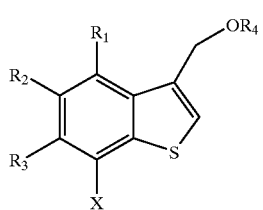

(IV)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_4$ is an acyl group, is reduced with a hydrogenating metal complex compound, basic hydrolysis, or acid hydrolysis.

8. A 3-hydroxymethyl-benzo[b]thiophene derivative represented by the formula (I):

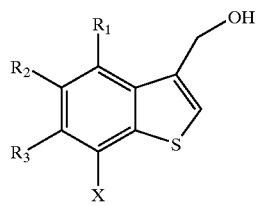

(I)

wherein $R_1$ is an alkyl group having 1 to 4 carbons, a trihalomethyl group, an alkoxy group having 1 to 4 carbons, an alkylthio group having 1 to 4 carbons, or a trihalomethoxy group; and $R_2$ and $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom.

9. A 3-hydroxymethyl-benzo[b]thiophene derivative according to claim 8 wherein X is a halogen atom, $R_1$ is an alkyl group having 1 to 4 carbons, and each of $R_2$ and $R_3$ is a hydrogen atom; or X is a halogen atom, $R_1$ and $R_2$ are, same or independently, an alkyl group having 1 to 4 carbons, and $R_3$ is a hydrogen atom in the above formula (I).

10. A method of producing a 3-hydroxymethyl-benzo[b] thiophene derivative represented by the formula (IV):

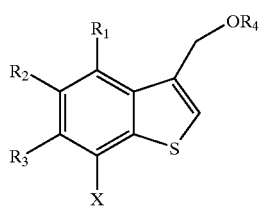

(IV)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; X is a halogen atom, a hydroxy group, or an acyloxy group having 1 to 9 carbons; and $R_4$ is an acyl group, comprising reacting a compound represented by the formula (III):

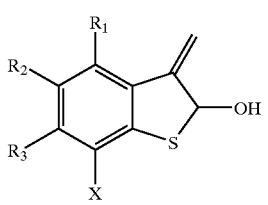

(III)

wherein $R_1$ to $R_3$ are, same or independently, a hydrogen atom, an alkyl group having 1 to 4 carbons, a trihalomethyl group, an alkoxy group having 1 to 4 carbons, an alkylthio group having 1 to 4 carbons, or a trihalomethoxy group; and X is a halogen atom, a hydroxy group, or an acyloxy group having 1 to 9 carbons, with one or more of carboxylic acid anhydride or carboxylic acid.

11. The method of producing a benzo[b]thiophene derivative according to claim 10 wherein $R_1$ to $R_3$ are, same or independently, a hydrogen atom, an alkyl group having 1 to 4 carbons, or a trihalomethyl group; and X is a halogen atom in the above formula (III).

12. A benzo[b]thiophene derivative represented by the formula (IV):
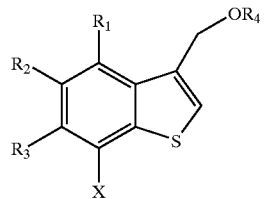
(IV)
wherein X is a halogen atom, $R_4$ is a trifluoroacetyl group, and $R_1$ is an alkyl group having 1 to 4 carbons, $R_2$ and $R_3$ are a hydrogen atom, or $R_1$ and $R_2$ are, together or independently, an alkyl group having 1 to 4 carbons, and $R_3$ is a hydrogen atom.
* * * * *